(12) United States Patent
Chalfant

(10) Patent No.: US 11,096,743 B2
(45) Date of Patent: *Aug. 24, 2021

(54) REMOTE CONTROL SWITCH FOR A LASER SYSTEM

(71) Applicant: THE SPECTRANETICS CORPORATION, Colorado Springs, CO (US)

(72) Inventor: Kenneth Chalfant, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 523 days.

This patent is subject to a terminal disclaimer.

(21) Appl. No.: 16/009,956

(22) Filed: Jun. 15, 2018

(65) Prior Publication Data

US 2018/0289420 A1    Oct. 11, 2018

Related U.S. Application Data

(63) Continuation of application No. 14/700,576, filed on Apr. 30, 2015, now Pat. No. 9,999,468.

(60) Provisional application No. 62/004,653, filed on May 29, 2014.

(51) Int. Cl.
*A61B 18/20* (2006.01)
*A61B 90/98* (2016.01)
(Continued)

(52) U.S. Cl.
CPC .............. *A61B 18/20* (2013.01); *A61B 90/98* (2016.02); *A61B 18/24* (2013.01);
(Continued)

(58) Field of Classification Search
CPC .................... A61B 18/20; A61B 90/98; A61B 2017/00199; A61B 2017/00973;
(Continued)

(56) References Cited

U.S. PATENT DOCUMENTS 4,862,886 A    9/1989   Clarke
7,563,259 B2 *  7/2009   Takahashi .............. A61B 17/00
                                                       606/1

(Continued)

*Primary Examiner* — Rene T Towa

(57) ABSTRACT

A laser system for use in an environment is disclosed. The laser system may include a base unit including a laser, a controller operatively coupled to the laser, and a first antenna operatively coupled to the controller. The laser system may further include a laser energy delivery system having a first end which receives laser energy from the laser and a second end which delivers the laser energy to the environment. The laser system may further include a switch unit located remote from the base unit and including a switch controller, a second antenna operatively coupled to the switch controller, and a user operable switch. The switch unit may be connected to the base unit through a tether. The controller may determine when the laser energy is provided to the laser energy delivery system based on a signal from the switch unit, the signal being sent wirelessly to the controller from the second antenna of the switch unit to the first antenna of the base unit.

16 Claims, 7 Drawing Sheets

(51) Int. Cl.
    *A61B 18/24*      (2006.01)
    *A61B 18/00*      (2006.01)
    *A61B 17/00*      (2006.01)
(52) U.S. Cl.
    CPC ........... *A61B 2017/00199* (2013.01); *A61B 2017/00221* (2013.01); *A61B 2017/00973* (2013.01); *A61B 2018/00577* (2013.01)
(58) Field of Classification Search
    CPC ........... A61B 2017/00115; A61B 2017/00221; A61B 2018/00577; A61B 18/24; A61B 2017/00017
    See application file for complete search history.

(56) References Cited

U.S. PATENT DOCUMENTS

| | | | |
|---|---|---|---|
| 2003/0195644 A1 | 10/2003 | Borders | |
| 2004/0115591 A1* | 6/2004 | Warner | A61C 1/0023 433/98 |
| 2006/0079768 A1* | 4/2006 | Small | A61M 5/14546 600/432 |
| 2006/0116667 A1* | 6/2006 | Hamel | A61B 17/320068 606/1 |
| 2006/0219049 A1* | 10/2006 | Horvath | A61B 17/00 74/560 |
| 2007/0166662 A1 | 7/2007 | Lint | |
| 2008/0125705 A1* | 5/2008 | Sato | A61B 18/1492 604/93.01 |
| 2008/0154249 A1* | 6/2008 | Cao | A61B 18/20 606/10 |
| 2009/0115578 A1* | 5/2009 | Geissler | H04Q 9/00 340/10.1 |
| 2009/0200283 A1* | 8/2009 | Bland | B23K 9/1087 219/132 |
| 2012/0161721 A1* | 6/2012 | Neethimanickam | H02J 50/70 320/167 |
| 2012/0191162 A1* | 7/2012 | Villa | A61N 5/06 607/89 |

* cited by examiner

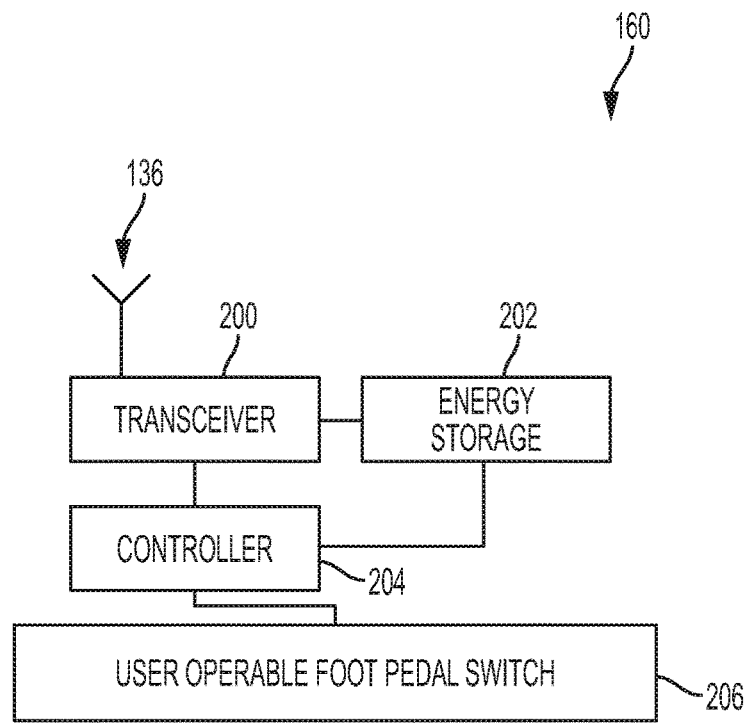
FIG. 3
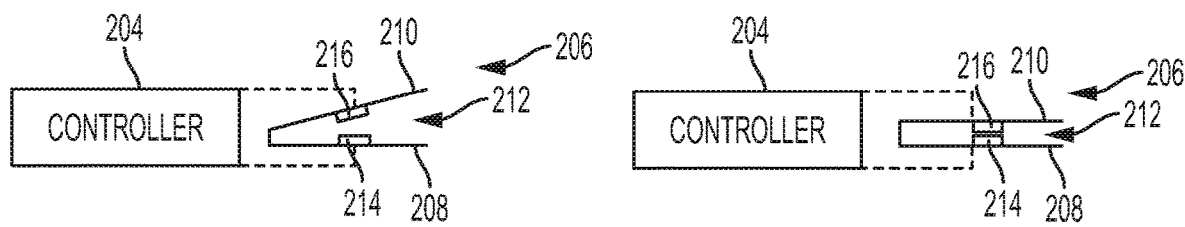
FIG. 4                    FIG. 5

REMOTE CONTROL SWITCH FOR A LASER SYSTEM

CROSS-REFERENCE TO RELATED APPLICATION

The present application is a continuation of U.S. application Ser. No. 14/700,576, filed Apr. 30, 2015, now U.S. Pat. No. 9,999,468, entitled REMOTE CONTROL SWITCH FOR A LASER SYSTEM, which claims the benefit of and priority to, under 35 U.S.C. § 119(e), U.S. Provisional Application Ser. No. 62/004,653, filed May 29, 2014, entitled REMOTE CONTROL SWITCH FOR A LASER SYSTEM, which are hereby incorporated by reference in their entireties for all purposes.

FIELD

The present disclosure relates generally to devices, methods and systems for controlling a laser system, and more specifically, to devices, methods, and systems for controlling a laser system of a laser ablation system for use in ablating tissue.

BACKGROUND

Laser systems are known for use in minimally invasive interventional procedures within the cardiovascular system of a patient or for other procedures.

SUMMARY

In an exemplary embodiment of the present disclosure, a laser system for use in an environment. The laser system comprising a base unit including a laser, a controller operatively coupled to the laser, and a first antenna operatively coupled to the controller. The laser system further comprising a laser energy delivery system having a first end which receives laser energy from the laser and a second end which delivers the laser energy to the environment. The laser system further comprising a switch unit located remote from the base unit and including a switch controller, a second antenna operatively coupled to the switch controller, and a user operable switch. The switch unit being connected to the base unit through a tether. The controller determines when the laser energy is provided to the laser energy delivery system based on a signal from the switch unit. The signal being sent wirelessly to the controller from the second antenna of the switch unit to the first antenna of the base unit. In one example, the user operable switch is a foot switch. In another example, the switch controller is an RFID tag. In a variation thereof, the RFID tag is a passive RFID tag. In another variation thereof, the switch controller receives a wireless call signal from the controller. Further, the signal being sent wirelessly to the controller from the second antenna of the switch unit includes a first response corresponding to the user operable switch being in a first state and a second response corresponding to the user operable switch being in a second state. In a refinement thereof, the user operable switch is a foot switch and the first state corresponds to the foot switch being depressed and the second state corresponds to the foot switch being undepressed. In a further refinement thereof, the controller permits the laser energy to be provided to the laser energy delivery system in response to receiving the first response from the switch unit and restricts the laser energy from being provided to the laser energy delivery system is response to receiving the second response from the switch unit. In a further refinement thereof, the RFID tag is a passive RFID tag. In a still further refinement thereof, the tether is devoid of any communication path operatively coupling the controller and the switch controller. In yet a further refinement thereof, the laser energy delivery system is a catheter system including at least one fiber optic cable which transports the laser energy from the first end of the laser energy delivery system towards the second end of the laser energy delivery system. In a further example, the tether is devoid of any communication path operatively coupling the controller and the switch controller. In still a further example, the laser energy delivery system is a catheter system including at least one fiber optic cable which transports the laser energy from the first end of the laser energy delivery system towards the second end of the laser energy delivery system. In yet still a further example, the controller sends a call signal to the switch unit to request a status of the user operable switch and the switch controller is powered with a portion of the energy of the call signal.

In another exemplary embodiment of the present disclosure, a method of operating a laser ablation system is provided. The laser ablation system including a base unit including a laser and a controller, a laser energy delivery system having a first end which receives laser energy from the laser and a second end which delivers the laser energy to the environment, and a switch unit located remote from the base unit and including a switch controller and a user operable switch having a first state and a second state. The method comprising the steps of sending a first wireless signal from the base unit to the switch unit; receiving a second wireless signal from switch unit at the base unit; and controlling a communication of laser energy from the laser to the laser energy delivery system in response to the received second wireless signal. When the second wireless signal indicates that the user operable switch is in a first state laser energy is permitted to travel through the laser energy delivery system towards the second end of the laser energy delivery system. When the second wireless signal indicates that the user operable switch is in a second state laser energy is restricted from travel through the laser energy delivery system towards the second end of the laser energy delivery system.

In a further exemplary embodiment of the present disclosure, a base unit of a laser system for use in an environment is provided. The laser system including a switch unit located remote from the base unit and a laser energy delivery system having a first end adapted to be coupled to the base unit to receive laser energy from the laser and a second end which delivers the laser energy to the environment. The switch unit including a switch controller, a second antenna operatively coupled to the switch controller, and a user operable switch. The base unit comprising a housing; a plurality of wheels supporting the housing; a laser housed in the housing; a controller operatively coupled to the laser; and a first antenna operatively coupled to the controller. The controller determines when the laser energy is provided to the laser energy delivery system based on a signal received from the switch unit, the signal being received wirelessly by the first antenna of the base unit. In one example, the signal is received in response to a call signal being sent by the controller through the first antenna.

In yet a further exemplary embodiment of the present disclosure, a switch unit of a laser system for use in an environment is provided. The laser system including a base unit located remote from the switch unit and a laser energy delivery system having a first end adapted to be coupled to the base unit to receive laser energy from the laser and a second end which delivers the laser energy to the environment. The switch unit comprising a switch controller, a second antenna operatively coupled to the switch controller, and a user operable switch. The switch controller sends a signal through the second antenna which provides an indication of a state of the user operable switch. In one example, the user operable switch is a foot pedal switch having a first state wherein a pedal of the foot pedal switch is depressed and a second state wherein the pedal of the foot pedal switch is undepressed. In another example, the signal is sent in response to a reception of a call signal from the base unit through the second antenna. In a variation thereof, the switch unit further comprises an energy storage device operatively coupled to the second antenna and operatively coupled to the switch controller. The energy storage device receives power from the second antenna and provides power to the switch controller.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "computer-readable medium" as used herein refers to any storage and/or transmission medium that participate in providing instructions to a processor for execution. Such a medium is commonly tangible and non-transient/non-transitory and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

The above and other features of the present disclosure, which alone or in any combination may comprise patentable subject matter, will become apparent from the following description and the attached drawings.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 3 illustrates an exemplary embodiment of a switch controller of the exemplary laser system of FIG. 1;

FIG. 4 illustrates a representation of a user operable foot switch in an undepressed state;

FIG. 5 illustrates the user operable foot switch of FIG. 4 in a depressed state;

Figure 1:
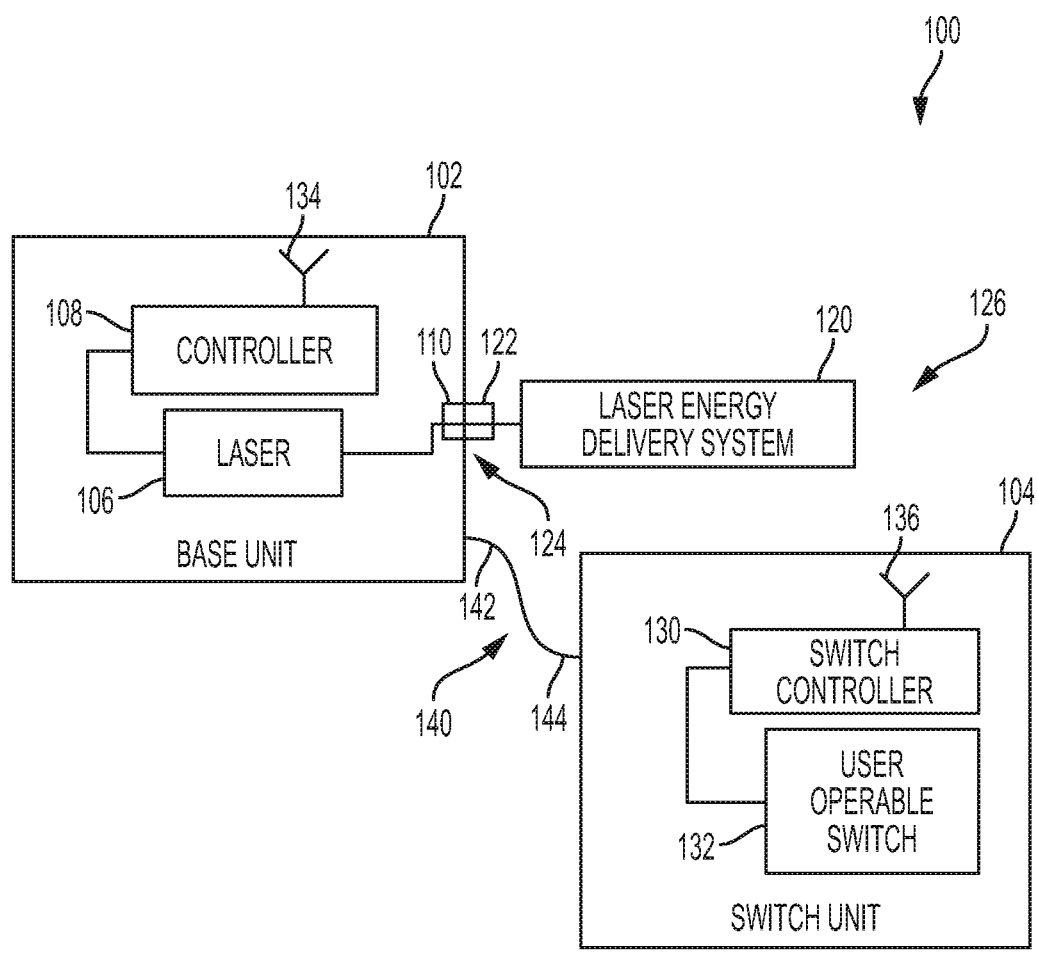
FIG. 1 illustrates an exemplary laser system including a base unit and a switch unit.

Corresponding reference characters indicate corresponding parts throughout the several views. It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION OF THE DRAWINGS

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to a laser ablation system, it should be understood that the features disclosed herein may have application to other laser systems having a switch unit remote from a base unit.

Referring to FIG. 1, an exemplary laser system 100 is shown. Laser system 100 includes a base unit 102 and a switch unit 104. Base unit 102 includes a laser 106 and a controller 108 operatively coupled to laser 106. Controller 108 controls the operation of laser 106 and when laser energy produced by laser 106 is communicated to an output port 110 of base unit 102.

As illustrated in FIG. 1, a laser energy delivery system 120 includes a coupler 122 which couples to output port 110 of base unit 102. Laser energy delivery system 120 includes one or more transport members which transport the received laser energy at a first end 124 of laser energy delivery system 120 towards a second end 126 of laser energy delivery system 120. Exemplary transport members include fiber optic cables. When the laser energy reaches second end 126 of laser energy delivery system 120 the laser energy is delivered to the surrounding environment. Laser energy delivery system 120 may include one or more features which alter an intensity, polarization, or focus of the laser energy. In one embodiment, the laser delivery energy system 120 focuses the laser energy at one or more points beyond the second end 126 of laser energy delivery system 120. In one embodiment, the laser energy delivery system 120 is a laser catheter device or assembly which may include laser catheters and/or laser sheaths. Examples of laser catheters or laser sheath are sold by the Spectranetics Corporation under the tradenames ELCA™ and Turbo Elite™ (each of which is used for coronary intervention or catheterization such as recanalizing occluded arteries, changing lesion morphology, and facilitating stent placement) and SLSII™ and Glide-Light™ (which is used for surgically implanted lead removal). The working (distal) end of a laser catheter typically has a plurality of laser emitters that emit energy and ablate the targeted tissue. The opposite (proximal) end of a laser catheter typically has a fiber optic coupler, which connects to a laser system or generator. One such example of a laser system is the CVX-300 Excimer Laser System, which is also sold by the Spectranetics Corporation.

Switch unit 104 includes a switch controller 130 and a user operable switch 132. User operable switch 132 receives an input from a user. Exemplary user operable switches include toggle switches, foot operated pedal switches, rotary switches, button switches, and other devices through which a user can provide an input.

Switch unit 104 is coupled to base unit 102 through a tether 140. A first end 142 of tether 140 is shown coupled to base unit 102 and a second end 144 of tether 140 is shown coupled to switch unit 104. In one embodiment, switch unit 104 may be stored within a compartment of base unit 102 when not in use and positioned remote from base unit 102 when laser system 100 is being used. In this embodiment, first end 142 of tether 140 is anchored inside of the storage compartment of base unit 102.

Tether 140 keeps switch unit 104 within an area surrounding base unit 102 and prevents switch unit 104 from being separated from base unit 102. In one embodiment, tether 140 is devoid of any power lines and/or communication lines. In an alternative embodiment, tether 140 may include one or both of a power line or communication line. An exemplary tether is a jacketed, flexible, steel wire safety cable. Other exemplary tethers include rope, wire, and other flexible members.

As illustrated in FIG. 1, base unit 102 includes an antenna 134 operatively coupled to controller 108 of base unit 102. In addition, an antenna 136 is operatively coupled to switch controller 130 of switch unit 104. In one embodiment, both controller 108 and switch controller 130 are configured to send and receive wireless signals to and from the other of controller 108 and switch controller 130 through the respective antennas 134 and 136. For example, in one embodiment controller 108 includes a radio-frequency identification ("RFID") transponder which sends call or interrogation signals and listens for responses and switch controller 130 includes one or more RFID tags which receive the call or interrogation signals from controller 108 and respond with a response signal. Exemplary response signals, include an identification number or indicator and/or data regarding a status of a device. In one embodiment, the response signal includes an indication of the state of user operable switch 132. Although RFID technology is discussed as an example other wireless technology may be implemented.

Figure 2:
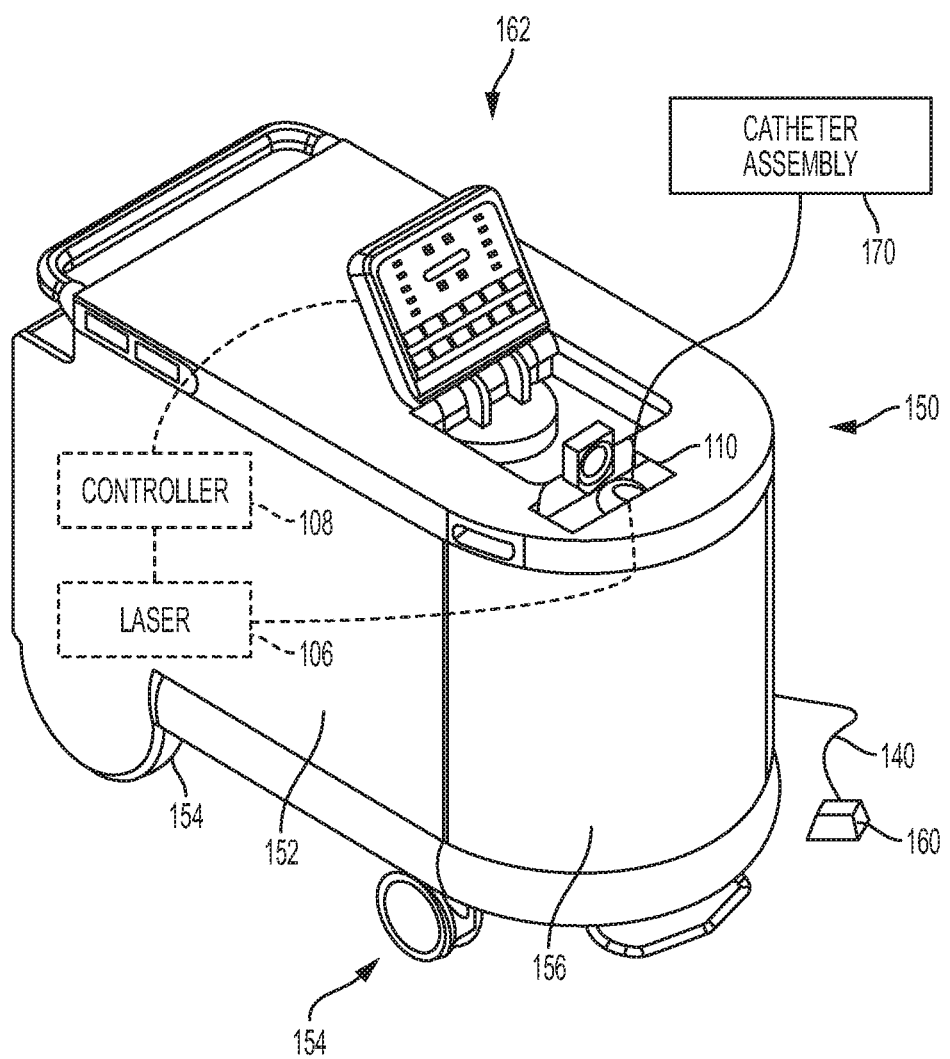
FIG. 2 illustrates an exemplary laser ablation system for use in ablating tissue in interventional procedures within the cardiovascular system of a patient including a base unit and a switch unit.

Referring to FIG. 2, an exemplary base unit 150 is shown. Exemplary base unit 150 includes a housing 152 which is supported by a plurality of wheels 154. Housing 152 houses laser 106 and controller 108. An exemplary base unit is the CVX-300 laser ablation system available from The Spectranetics Corporation located at 9965 Federal Drive in Colorado Springs, Colo. 80921. An exemplary laser ablation system is described in U.S. Pat. No. 5,383,199, the entire disclosure of which is expressly incorporated by reference herein. A catheter assembly 170 may be coupled to exemplary base unit 150 to receive laser energy from laser 106. The catheter assembly 170 serves as an exemplary laser energy delivery system 120 and communicates the laser energy to a desired location. Exemplary catheter assembly 170 are disclosed in U.S. Pat. No. 5,267,993, the entire disclosure of which are expressly incorporated by reference herein.

Further exemplary catheter assemblies are disclosed in co-pending application Ser. No. 13/804,812, filed Mar. 14, 2013, titled INTELLIGENT CATHETER, the entire disclosure of which is expressly incorporated by reference herein ("812 Application"). The catheter assemblies disclosed in the 812 Application include RFID technology and communicate with an RFID unit provided on the base unit. In one embodiment, a system is provided utilizing the herein disclosed switch units, the catheter assemblies disclosed in the 812 Application, and an RFID unit on the base unit including the functionality disclosed herein and disclosed in the 812 Application.

Returning to FIG. 2, housing 152 further includes a door 156 which provides access to a storage compartment. An exemplary switch unit 160 may be stored in the storage compartment when not in use. As shown in FIG. 2, switch unit 160 is coupled to base unit 150 through a tether 140. Since tether 140 does not include any power cables or communication cables, in the event that exemplary base unit 150 is rolled over tether 140 there would be no interruption to the power supplied from base unit 150 to switch unit 160 nor in the ability to exchange communications between base unit 150 and switch unit 160.

Base unit 150 further includes a control panel 162 supported by wheels 154. Through control panel 162 an operator is able to activate and control the operation of laser 106 through controller 108. As explained herein, controller 108 controls the operation of laser 106 at least in part based on an indication of the state of user operable switch 132 of switch unit 160.

Referring to FIG. 3, an exemplary embodiment of switch unit 160 is shown. Switch controller 130 includes a transceiver 200 which receives a call signal from controller 108 through antenna 136. A portion of the received energy is used to charge an energy storage device 202. Exemplary energy storage devices include capacitors. A controller 204 is powered by the energy stored in energy storage device 202. Controller 204 monitors the state of a user operable foot pedal switch 206. In the illustrated embodiment, switch unit 160 is a passive device meaning that the power used to operate switch unit 160 to generate a response signal is derived from the energy in the received call signal. In an alternative embodiment, switch unit 160 is an active device and includes a battery or other power source.

Referring to FIGS. 4 and 5, a representation of pedal switch 206 is shown. Pedal switch 206 includes a base 208, a pedal 210 moveable relative to base 208, and a switch 212 which provides an indication of a position of pedal 210 relative to base 208. As shown in FIG. 4, pedal 210 is rotated upward relative to base 208. As shown in FIG. 5, pedal 210 is rotated downward relative to base 208.

Base 208 carries a first contact 214. Pedal 210 carries a second contact 216. When contacts 214 and 216 are in contact (see FIG. 5) pedal switch 206 is in a first state. When contacts 214 and 216 are spaced apart (see FIG. 4), pedal switch 206 is in a second state. Controller 204 monitors whether pedal switch 206 is in the first state or the second state. For example, the opening or closing of switch 206 may change an input voltage to the controller 204. When an operator wants to communicate laser energy from laser 106 to the distal end of catheter assembly 170, the operator would push down on pedal 210. When the operator wants to prevent communication of laser energy from laser 106 to the distal end of catheter assembly 170, the operator would release the downward pressure on pedal 210. Although contacts 214 and 216 are illustrated as switch 212, other switches may be implemented.

Figure 9:
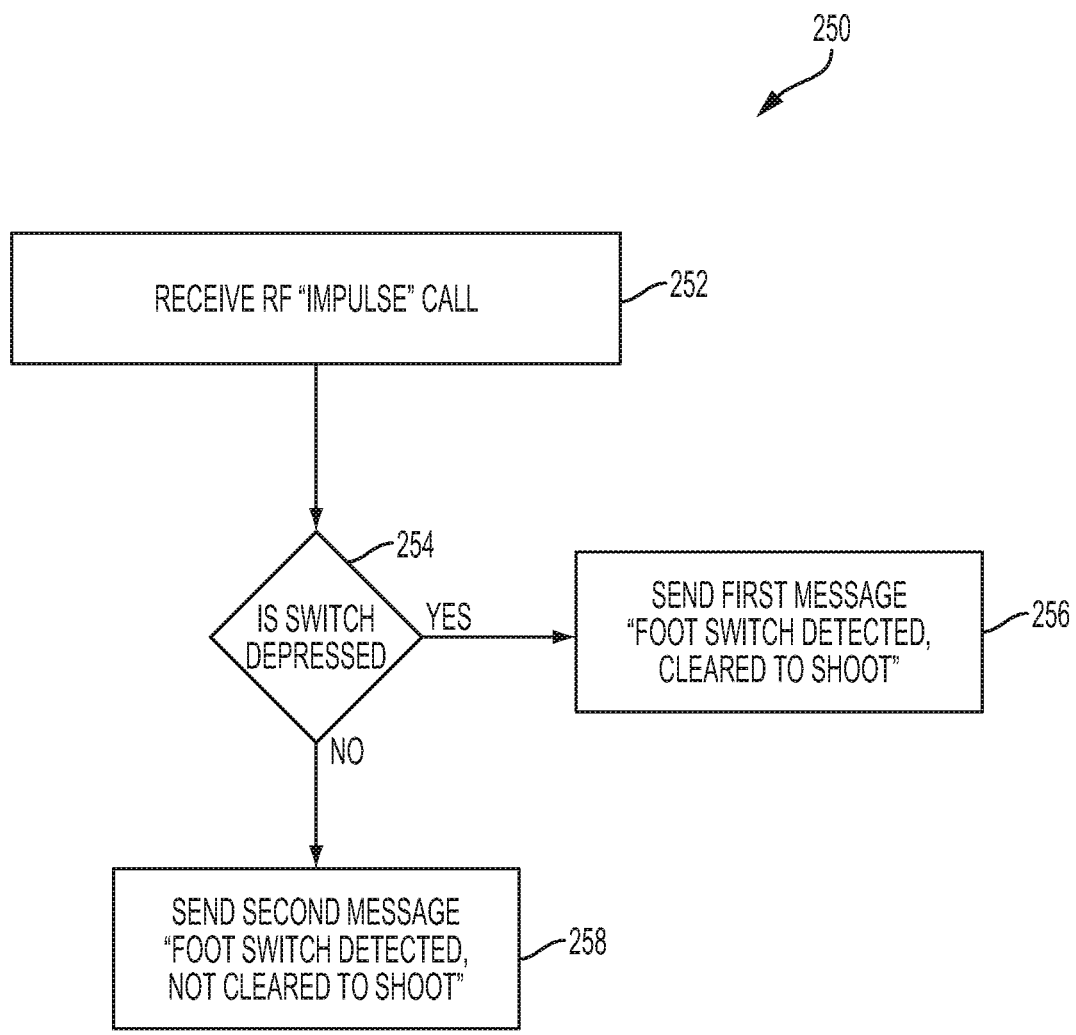
FIG. 9 illustrates an exemplary processing sequence of the switch unit of the laser ablation system of FIG. 3.

Referring to FIG. 9, an exemplary processing sequence 250 for controller 204 is provided. Switch unit 160 receives a call signal from controller 108, as represented by block 252. The call signal is used to power controller 204. Controller 204 determines the state of pedal switch 206, as represented by block 254. If controller 204 determines that pedal switch 206 is in the first state (see FIG. 5), controller 204 sends a first response message to controller 108 through antenna 136 that provides an indication that pedal switch 206 is currently depressed, as represented by block 256. If controller 204 determines that pedal switch 206 is in the second state (see FIG. 4), controller 204 sends a second response message to controller 108 through antenna 136 that provides an indication that pedal switch 206 is not currently depressed, as represented by block 258.

In one embodiment, two passive RFID tags are used in conjunction with pedal switch 206. In this embodiment, when pedal switch 206 is in the first state (FIG. 5) a first RFID tag is active and responds to the call signal from controller 108, while a second RFID tag is inactive, and when pedal switch 206 is in the second state (FIG. 4) the first RFID tag is inactive and the second RFID tag is active and responds to the call signal from controller 108. For example, the open state or closed state of contacts 214 and 216 may alter the provision of power from antenna 136 to the respective controller 204 of each RFID tag. In this embodiment, the individual controllers 204 do not need to determine the state of pedal switch 206. Rather, the state of pedal switch 206 may be inferred by which RFID tag responds to the call signal from controller 108.

Figure 6:
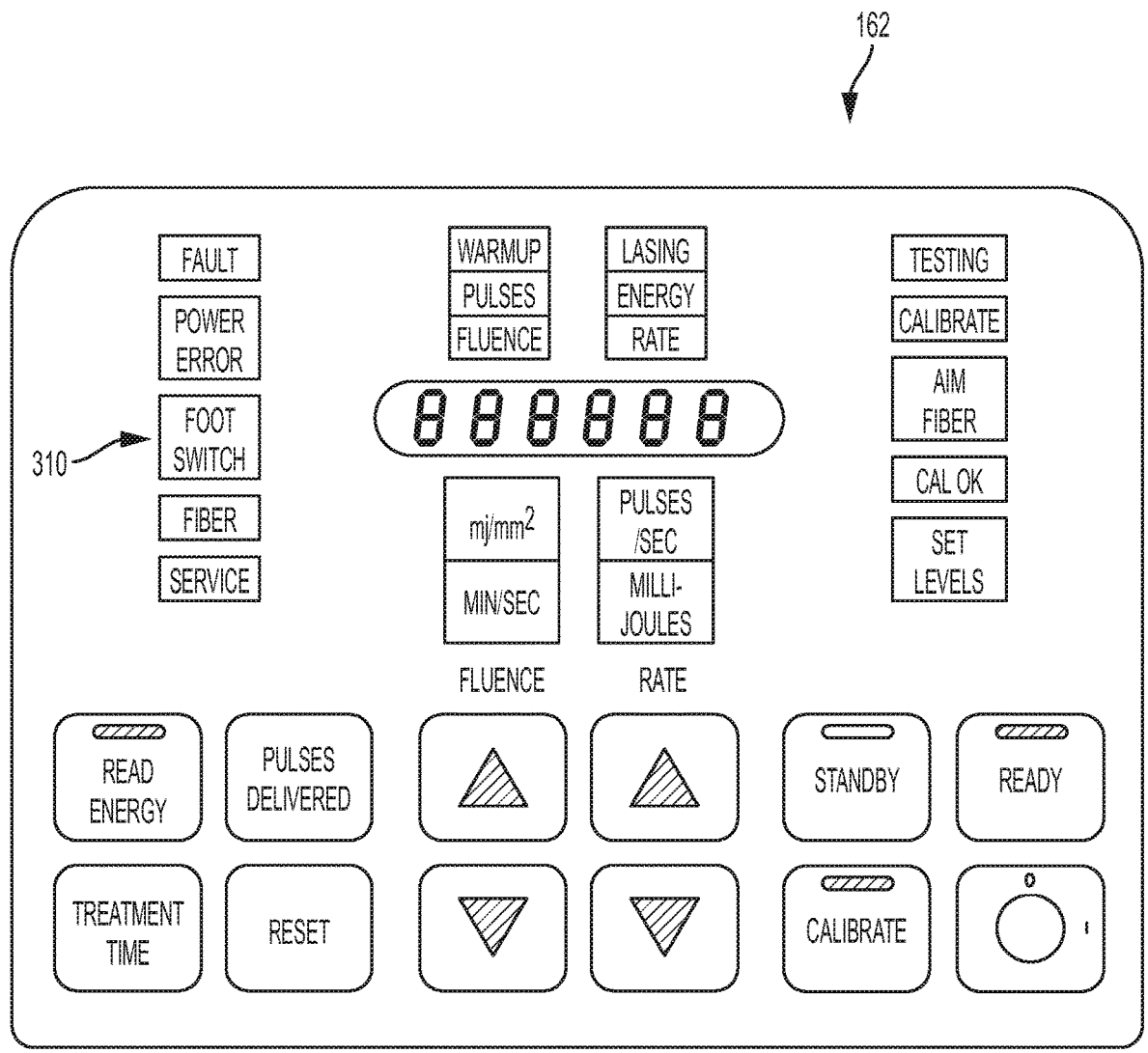
FIG. 6 illustrates an exemplary control panel of the laser ablation system of FIG. 3.
Figure 7:
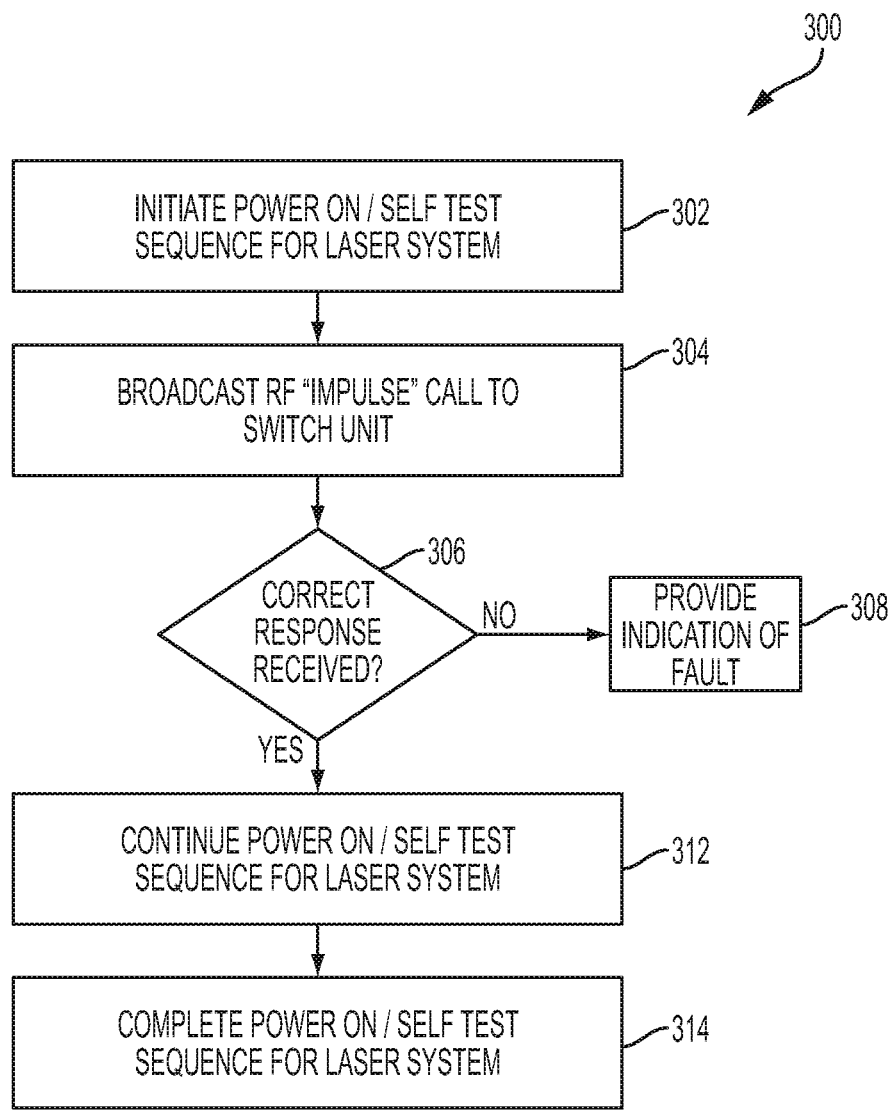
FIG. 7, illustrates an exemplary processing sequence of a controller of the laser ablation system of FIG. 3.

Referring to FIG. 7, an exemplary processing sequence 300 of controller 108 is shown. Processing sequence 300 corresponds to a power on or self test sequence for exemplary base unit 150. The power on or self test sequence for exemplary base unit 150 is initiated, as represented by block 302. Controller 108 sends a call signal through antenna 134 to make sure pedal switch 206 is in the second state (see FIG. 4), as represented by block 304. Controller 108 determines if the response received back is indicative of pedal switch 206 being in the second state, as represented by block 306. If pedal switch 206 is in the first state then controller 108 provides an indication of a fault, as represented by block 308. In one embodiment, controller 108 illuminates a light 310 on control panel 162 (see FIG. 6) to indicate the presence of a fault. In one example, controller 108 also stops the power on or self test sequence until the fault is corrected. Other exemplary indications include visual indications, audible indications, tactile indications, or combinations thereof. If pedal switch 206 is in the second state, controller 108 continues with the power on or self test sequence, as represented by block 312, and completes the power on or self test sequence, as represented by block 314.

Figure 8:
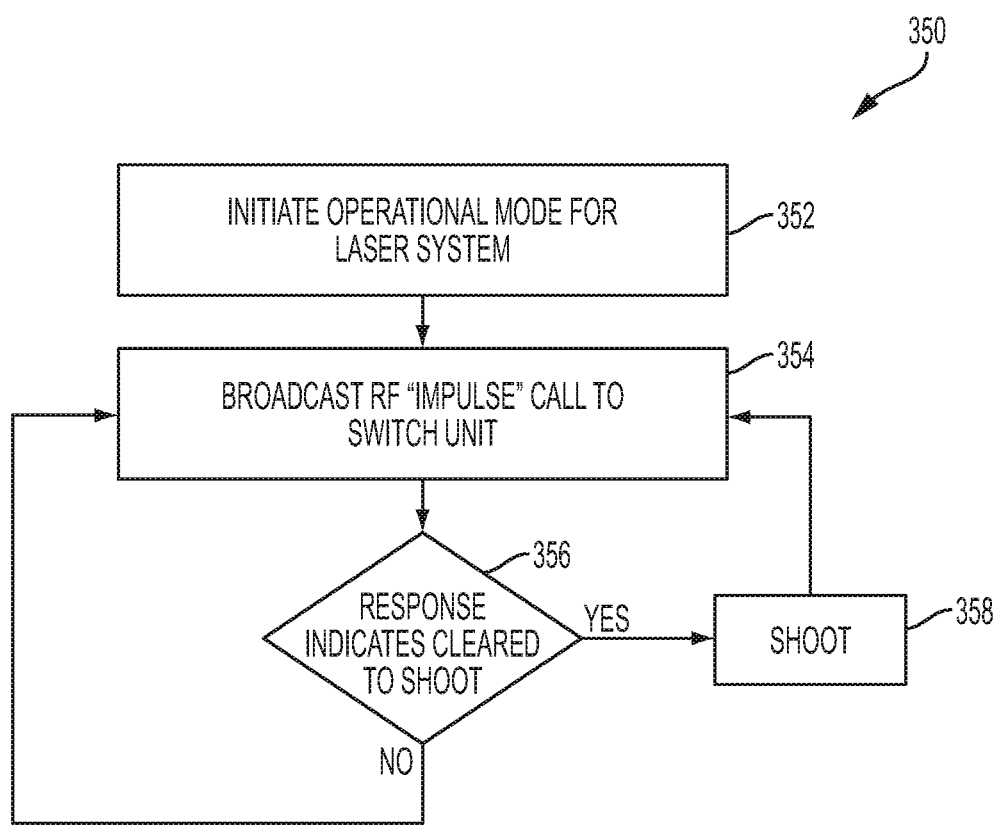
FIG. 8 illustrates another exemplary processing sequence of the controller of the laser ablation system of FIG. 3.

Referring to FIG. 8, an exemplary processing sequence 350 of controller 108 is shown. Processing sequence 350 corresponds to an operational mode sequence for exemplary base unit 150. Exemplary operational modes include the firing of laser 106 or the communication of laser energy from laser 106 to catheter assembly 170. One exemplary operational mode is the communication of laser energy through catheter assembly 170 to ablate tissue near the distal tip of catheter assembly 170.

The operational mode sequence for exemplary base unit 150 is initiated, as represented by block 352. Prior to firing laser 106, controller 108 sends a call signal through antenna 134 to make sure pedal switch 206 is in the first state (see FIG. 5), as represented by block 354. Controller 108 determines if the response received back is indicative of pedal switch 206 being in the first state, as represented by block 356. If pedal switch 206 is in the first state then controller 108 fires or shoots a pulse of laser energy from laser 106 through catheter assembly 170, as represented by block 358. If the response received back is indicative of pedal switch 206 being in the second state, controller 108 again sends out a call signal as represented by block 354. In one embodiment, controller 108 verifies that pedal switch 206 is in the first state prior to each pulse of energy being fired from laser 106. As such, if a caregiver wants to fire multiple pulses of energy in a row, the caregiver must maintain the pedal switch 206 in the first state. In one embodiment, laser 106 is a pulsed ultraviolet laser with a firing repetition rate of 80 Hertz and controller 108 verifies the position of pedal switch 206 at a higher repetition rate than 80 Hertz. In one embodiment, laser 106 is a pulsed ultraviolet laser with a firing repetition rate of 160 Hertz and controller 108 verifies the position of pedal switch 206 at a higher repetition rate than 160 Hertz.

A number of variations and modifications of the disclosure can be used. It would be possible to provide for some features of the disclosure without providing others.

For example, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a non-transient/non-transitory storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

While this invention has been described as relative to exemplary designs, the present invention may be further modified within the spirit and scope of this disclosure. Further, this application is intended to cover such departures from the present disclosure as come within known or customary practice in the art to which this invention pertains.

The invention claimed is:

1. A laser system for use in an environment, comprising:
a base unit including a laser and a base unit controller operatively coupled to the laser;
a laser energy delivery system having a first end which receives laser energy from the laser and a second end which delivers the laser energy to the environment; and
a switch unit located remote from the base unit and including:
a switch controller including a transceiver configured to receive a call signal from the base unit controller, a user operable switch, wherein the switch controller is capable of transmitting a response signal indicative of a state of the user operable switch, and
an energy storage device operatively coupled to the switch controller, wherein the energy storage device receives power from the call signal and provides power to the switch controller to generate the response signal, wherein the base unit controller determines when the laser energy is provided to the laser energy delivery system based on the response signal from the switch unit, the response signal being sent wirelessly from the switch unit to the base unit controller.

2. The laser system of claim 1, wherein the user operable switch is a foot switch.

3. The laser system of claim 1, wherein the switch controller comprises a first RFID tag and a second RFID tag, wherein the response signal is generated by the first RFID tag when the user operable switch is open, and wherein the response signal is generated by the second RFID tag when the user operable switch is closed.

4. The laser system of claim 1, wherein the laser energy delivery system is a catheter system including at least one fiber optic cable which transports the laser energy from the first end of the laser energy delivery system towards the second end of the laser energy delivery system.

5. The laser system of claim 1, wherein the laser energy delivery system is a catheter system including at least one fiber optic cable which transports the laser energy from the first end of the laser energy delivery system towards the second end of the laser energy delivery system.

6. The laser system of claim 1, wherein the base unit controller sends the call signal to the switch unit to request a status of the user operable switch and the switch controller is powered with at least a portion of the energy of the call signal to generate the response signal.

7. The laser system of claim 1, wherein the response signal being sent wirelessly from the switch unit to the base unit controller includes a first response corresponding to the user operable switch being in a first state and a second response corresponding to the user operable switch being in a second state.

8. The laser system of claim 7, wherein the user operable switch is a foot switch and the first state corresponds to the foot switch being depressed and the second state corresponds to the foot switch being undepressed.

9. The laser system of claim 8, wherein the base unit controller permits the laser energy to be provided to the laser energy delivery system in response to receiving the first response from the switch unit and restricts the laser energy from being provided to the laser energy delivery system in response to receiving the second response from the switch unit.

10. The laser system of claim 9, wherein the switch controller comprises a first RFID tag that produces the first response and a second RFID tag that produces the second response.

11. A switch unit of a laser system for use in an environment, the laser system including a base unit located remote from the switch unit and a laser energy delivery system having a first end adapted to be coupled to the base unit to receive laser energy from the laser and a second end which delivers the laser energy to the environment, the switch unit comprising:
  a switch controller including a transceiver for receiving a call signal from a base unit controller,
  a user operable switch, wherein the switch controller sends a response signal that provides an indication of a state of the user operable switch to the base unit, and
  an energy storage device operatively coupled to the switch controller, wherein the energy storage device receives power from the call signal and provides power to the switch controller to generate the response signal.

12. The switch unit of claim 11, wherein the user operable switch is a foot pedal switch having a first state wherein a pedal of the foot pedal switch is depressed and a second state wherein the pedal of the foot pedal switch is undepressed.

13. The switch unit of claim 11, wherein the switch controller comprises a first RFID tag and a second RFID tag, wherein the response signal is generated by the first RFID tag when the user operable switch is open, and wherein the response signal is generated by the second RFID tag when the user operable switch is closed.

14. The switch unit of claim 11, wherein the base unit controller sends the call signal to the switch unit to request a status of the user operable switch and the switch controller is powered with at least a portion of the energy of the call signal to generate the response signal.

15. The switch unit of claim 14 wherein the first and second RFID tags are configured to respond to the call signal from the base unit controller to produce the response signal.

16. The switch unit of claim 14 wherein the first and second RFID tags are configured to use energy from the call signal received from the base unit controller to produce the response signal.

* * * * *